United States Patent [19]
Rosenstatter

[11] Patent Number: 5,730,596
[45] Date of Patent: Mar. 24, 1998

[54] DENTAL INSTRUMENT HOLDER

[76] Inventor: Otto Rosenstatter, Matzing 105, A-5164 Seeham, Austria

[21] Appl. No.: 825,860

[22] Filed: Apr. 2, 1997

[30] Foreign Application Priority Data

Apr. 5, 1996 [DE] Germany ............ 196 13 680.6

[51] Int. Cl.$^6$ .................................. A61C 1/14
[52] U.S. Cl. ........................... 433/127; 433/129
[58] Field of Search .................. 433/127, 128, 433/129; 279/43.1, 43.2, 43.4, 46.3, 46.2

[56] References Cited

U.S. PATENT DOCUMENTS

| | | | |
|---|---|---|---|
| 4,436,512 | 3/1984 | Garcia | 433/129 |
| 4,536,157 | 8/1985 | Maizenberg | 433/129 |
| 4,611,990 | 9/1986 | Lares et al. | 433/129 |
| 5,254,004 | 10/1993 | Feldman et al. | 433/129 |
| 5,383,785 | 1/1995 | Brugger | 433/129 |

*Primary Examiner*—Nicholas D. Lucchesi

[57] ABSTRACT

A dental instrument holder (10) comprises a clamping sleeve (28) having two cylindrical annular closed bearing regions (50, 52) axially spaced apart is arranged in the driven hollow shaft (22) accommodating the dental instrument. A spring-loaded clamping region (56) is located between these cylindrical bearing regions (52, 54), which clamping region preferably has two spring tongues (62, 64) partitioned by a U-shaped incision or indent (58, 60) from the clamping sleeve (28). The clamping sleeve (28) and the structural part (22) adjacent thereto may execute a relative axial movement between two positions: in the first, the clamping position, the elastically spring-loaded clamping region (56) of the clamping sleeve (28) is pressed radially inwards by a conical actuating surface (70) provided on the structural part (22). In the other relative position, the release position, the spring-loaded clamping region (56) of the clamping sleeve (28) can disengage so that the shank of a dental instrument accommodated therein can thereby be released. The two bearing regions (50, 52) that are provided on both sides of the elastic clamping region (56) of the clamping sleeve no longer perform a bearing function, with the result that the bearing and mounting of the dental instrument within the head of the dental instrument holder (10) is more precise, imbalances and eccentricities are avoided, and in this way damage to the bearings (24, 26) of the hollow shaft (22) as well as to the dental instrument itself are largely excluded.

6 Claims, 3 Drawing Sheets

DENTAL INSTRUMENT HOLDER

BACKGROUND TO THE INVENTION

The present invention relates to a dental instrument holder or handpiece.

Dental instrument holders of the kind with which the present invention is concerned are known from for example U.S. Pat. No. 3074167, U.S. Pat. No. 4436512, and AT-396646. Relevant instrument holders comprise:

a) a housing comprising a head region and a handle region;

b) a driven hollow shaft rotatably mounted in the head region of the housing and designed to receive the shank of a dental instrument;

c) a clamping sleeve arranged within the hollow shaft into which sleeve the end region of the shank of the dental instrument can be inserted and which has at least one spring-loaded clamping region;

d) a conical actuating surface on a structural element adjacent to the clamping sleeve and which co-operates with the spring-loaded clamping region of the clamping sleeve, wherein e) the structural element carrying the conical actuating surface and the clamping sleeve can be moved in a reciprocating manner between two axial relative positions, namely ea) a clamping position in which the spring-loaded clamping region of the clamping sleeve is urged radially inwardly by the conical actuating surface;

eb) a release position in which the spring-loaded clamping region or the clamping sleeve is urged in a radial direction under the action of the spring.

Common to all these known instrument holders is the principle of clamping the shank of the dental instrument, for example a drill, within the hollow driving shaft in such way that an axial relative movement occurs between the clamping sleeve retaining the end of the instrument and the adjacent structural element. This relative movement is converted via the cam action of the correspondingly geometrically shaped actuating surface of the adjacent structural element into a radial movement of the spring-loaded clamping region of the clamping sleeve. The adjacent structural element together with the generally conical actuating surface is, in the instrument holders disclosed in the documents referred to above, the hollow shaft itself, and in the instrument holder known from the aforementioned AT-396646 is a separate actuating sleeve that can be displaced in an axial direction. The spring-loaded clamping region is however always formed at one end of the clamping sleeve, and to be more precise by a plurality of indents on the free edge of the clamping sleeve. These form in this way spring tongues whose free ends at the same time form the end of the clamping sleeve. The disadvantage of this design is that the spring-loaded clamping region to some extent always has to perform in addition bearing functions that are not particularly compatible with its spring-loaded property. As a result the shank of the dental instrument is not always mounted in an optimum manner within the instrument holder, which can lead to an imbalance or eccentricity. Given the very high running speeds of the hollow shaft in modern dental instrument holders, this imbalance can in turn lead to damage in the bearings or even to damage in the dental instrument.

SUMMARY OF THE INVENTION

The present invention provides an instrument holder of the kind referred to above in which the clamping sleeve has two axially spaced apart cylindrical annularly closed bearing regions, between which the spring-loaded clamping region is arranged.

The holder of the present invention has the advantage that the shank of the dental instrument can be mounted with the maximum precision, thereby avoiding imbalances and eccentricities and as a result damage to the bearings or to the dental instrument.

Furthermore, the provision of two axially spaced apart bearing regions on the clamping sleeve means that its spring-loaded clamping region can freed from any bearing function. The clamping region now only has to fulfil the single function, compatible with its elastically spring-loaded properties, of firmly clamping the end region of the shank of the instrument and also releasing it again in the corresponding relative position. The bearing function is undertaken by the annularly closed and thus essentially rigid bearing regions. As a result the shank of the dental instrument is guided with maximum precision within the clamping sleeve and thus also within the hollow shaft; imbalances and eccentricities and their already mentioned damaging consequences can thus be reliably avoided.

The spring-loaded clamping region of the clamping sleeve conveniently has at least one spring tongue that is cut out from the clamping sleeve in the form of a U-shaped incision or indent. The free ends of these spring tongues, in contrast to those of the prior art, no longer lie at the axial end of the clamping sleeve, with the result that their radial movement no longer influences the bearing properties of the clamping sleeve.

Two diametrically opposite spring tongues are conveniently provided. This symmetrical arrangement not only avoids imbalances within the clamping sleeve itself but also facilitates the reliable clamping of the shank of the dental instrument.

Each spring tongue can have at its free end a conical surface that co-operates with the conical actuating surface of the adjacent structural element. The conical surfaces should have at least approximately the same cone angle as the actuating surface, the relative movement between the clamping sleeve and the adjacent structural element thereby being facilitated.

Furthermore, a groove-shaped undercut or release groove is preferably provided on the larger diameter edge of the conical actuating surface of the structural element adjacent to the clamping sleeve. In the release position this groove-shaped undercut facilitates the complete spring disengagement of the elastic clamping region of the clamping sleeve, so that the shank of the dental instrument can easily be removed from the clamping sleeve.

In general, with the dental instrument holders of the type mentioned at the beginning a compression spring ensures that the respective axially movable part (clamping sleeve or its adjacent structural element) automatically adopts the clamping position. In this case it is recommended to employ an arrangement in which the compression spring is formed by a sleeve of a spring material through which a helical cut or incision is made. In this way particularly inexpensive and relatively robust and sturdy compression springs can be made that are particularly suited to transmit axial shear forces.

INTRODUCTION TO THE DRAWINGS

DESCRIPTION OF PREFERRED EMBODIMENTS

Figure 1:
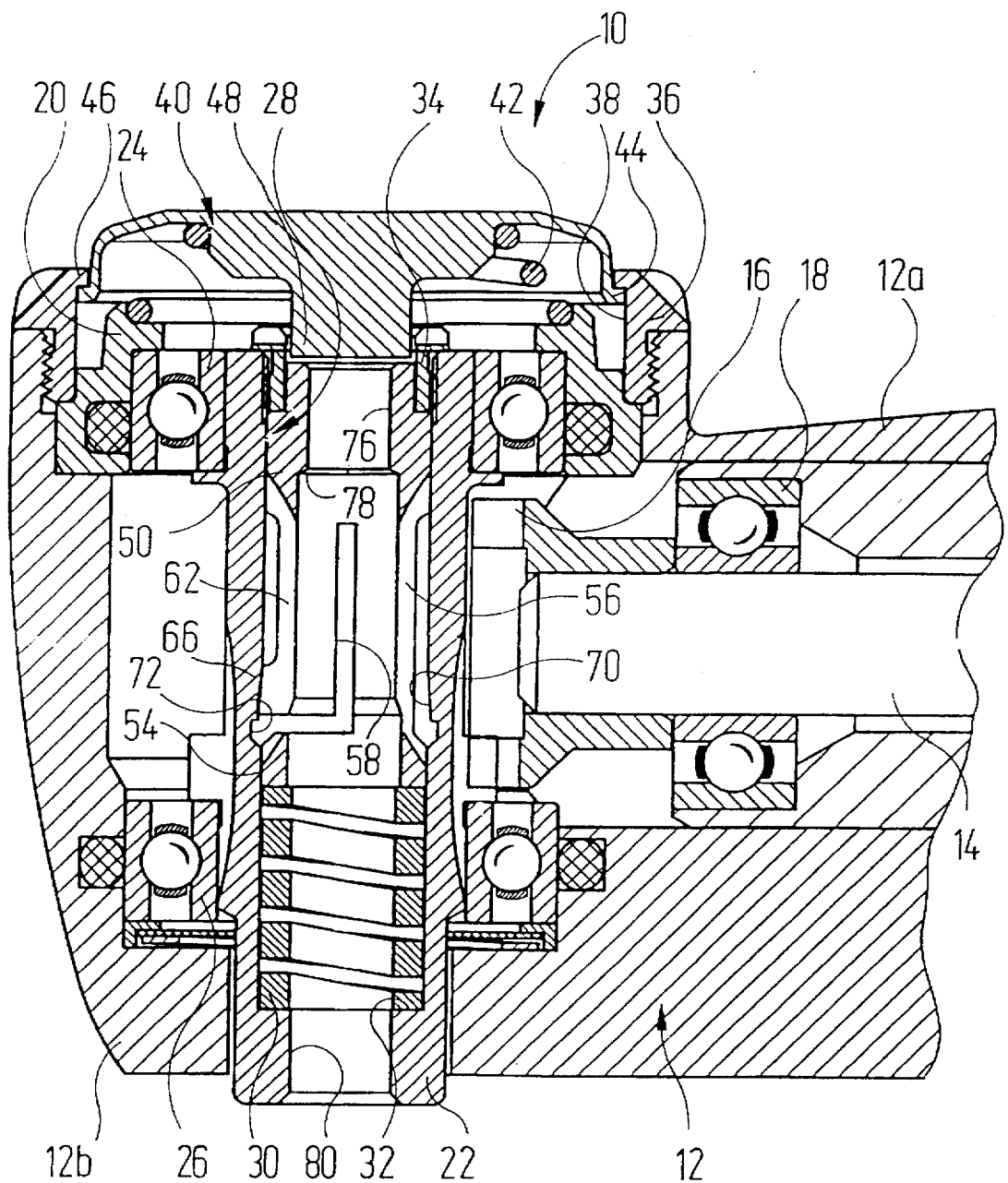
FIG. 1 is a partial section through a first embodiment of a dental instrument holder.

FIG. 1 is a partial section through a dental instrument holder, which is designated overall by the reference numeral 10. Its housing 12 comprises a handle region 12a, only part of which is shown in the diagram, and a head region 12b.

A drive shaft 14 passes in a manner known per se through the handle region 12a of the housing 12, the end of the drive shaft, which is shown in the diagram provided with a toothed gearwheel 16, being mounted in a ball bearing arrangement 18.

The upwardly open head region 12b of the housing 12 is closed by a removable cover 20, which is secured by means of a screw ring 36 to the head region 12b of the housing 12.

Furthermore, a hollow shaft 22 extends, likewise in a known manner, through the head region 12b of the housing 12, the said hollow shaft being rotatably held in the region of its upper end in a first ball bearing arrangement 24 secured in the cover 20, and in the region of its lower end in a second ball bearing arrangement secured in the head region 12b of the housing 12.

Figure 2:
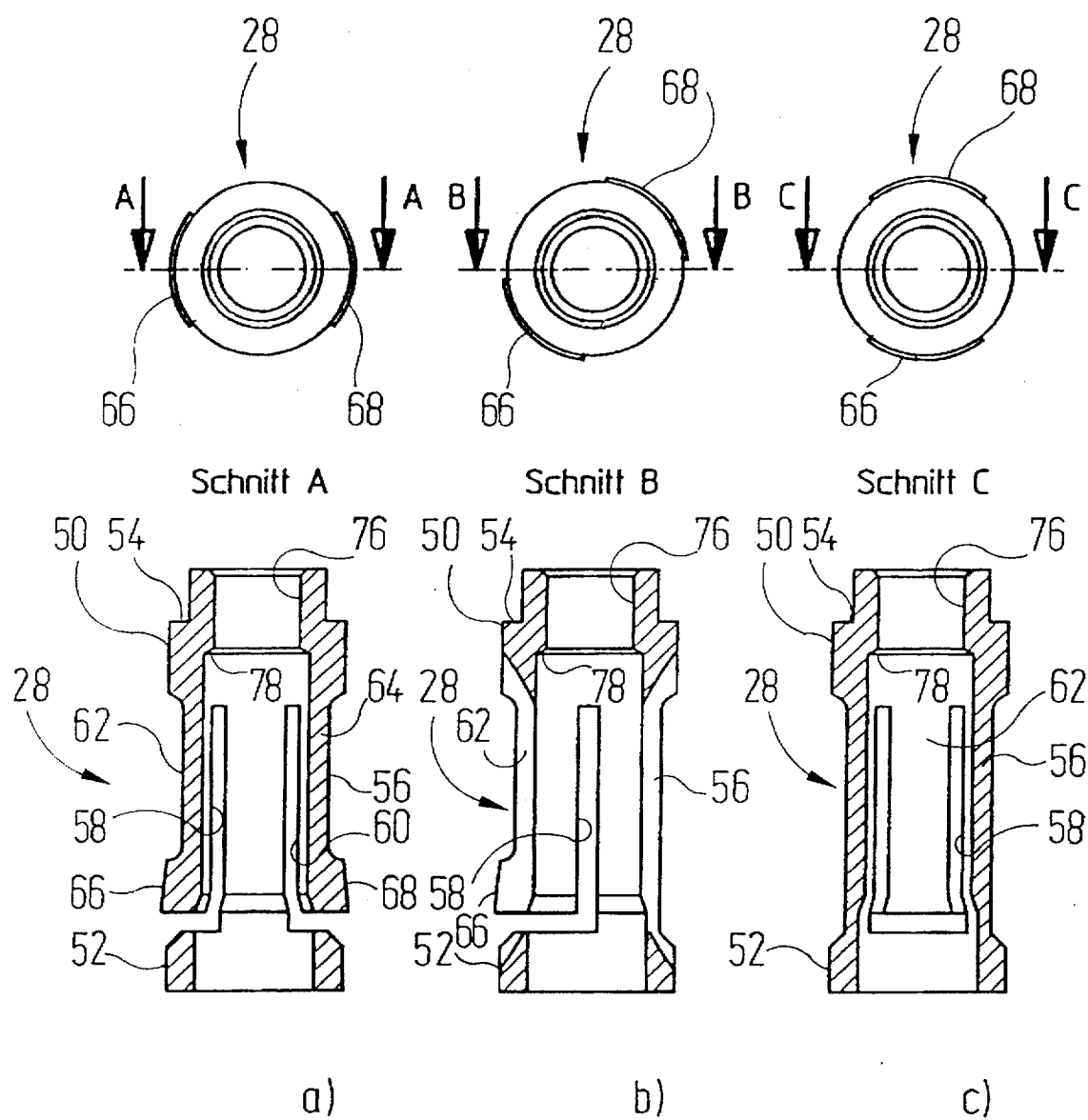
FIGS. 2a to 2c are axial sections through a clamping sleeve that is used in the dental instrument holder shown in FIG. 1, in each case together with the plan view, characterising the sectional plane, of the clamping sleeve.

The interior of the hollow shaft 22 accommodates, axially aligned with respect to one another, a clamping sleeve 28 whose exact construction is explained further below on the basis of FIG. 2, as well as a compression spring 30, whose manner of construction will likewise be discussed in more detail later and which is supported axially on a shoulder 32 in the interior of the hollow shaft 22. The clamping sleeve 28 is normally urged upwardly by means of the compression spring 30; its axial mobility in this direction is restricted by a stop ring 34 screwed into the hollow shaft 22.

A press button 40 is guided by the inner surface 38 of the screw ring 36, and is displaceable in the axial direction (referred to the axis of the hollow shaft 22). A compression spring 42 held between the lower side of the press button 40 and the upper side of the cover 20 urges the press button 40 upwardly so that normally a radially projecting edge region 44 of the press button 40 rests against a radially slightly inwardly projecting flange 46 of the screw ring 36. A centric, axially downwardly extending cylindrical projection or lug 48 is also formed on the press button 40, the lower front face of the projection co-operating with the upwardly directed front face of the clamping sleeve 28. This arrangement obviously operates so that, by pressing on the press button 40, the latter can be displaced downwardly under compression of the compression spring 42. Under this axial movement the cylindrical projection 48 of the press button 40 forces the clamping sleeve 28 axially downwardly against the action of the compression spring 30, whereby the clamping action of the clamping sleeve 28 is released to free the instrument driven by the hollow shaft 22, as is also described in more detail hereinbelow.

The exact construction of the clamping sleeve 28 is shown in more detail in FIGS. 2a to 2c, to which reference is now made. In the upper half of these Figures various sectional planes are defined in the plan view of the clamping sleeve 28; the lower half of these Figures shows the respective axial section through the clamping sleeve 28 in the corresponding sectional plane.

The clamping sleeve 28 comprises an upper cylindrical, annular closed bearing region 50 as well as a lower cylindrical, annular closed bearing region 52, whose external diameter in each case coincides with the internal diameter of the hollow shaft 22. A shoulder 54 that serves to accommodate the stop ring 34 can be seen in the external contour of the clamping sleeve 28, above the upper bearing region 50 (compare FIG. 1).

Between the upper and lower bearing regions 50 and 52, the clamping sleeve 28 is designed and formed as a spring-loaded clamping region 56. Two spring tongues 62, 64 are formed in the spring-loaded clamping region 56 of the clamping sleeve by two diametrically opposite U-shaped incisions or cuts 58 and 60 passing through the wall of the clamping sleeve 28.

The lower ends of the spring tongues 62 and 64, which can move radially to a certain extent by elastic bending of the said spring tongues 62, 64, are provided with outer conical surfaces 66 and 68, the largest radius of the conical surfaces 66, 68 being on the lower edge of the spring tongues 62, 64. This largest radius of the conical surfaces 66, 68 is somewhat larger than the radius of the bearing regions 50 and 52 of the clamping sleeve 28, as can also be seen in particular from the plan view, in each case illustrated in the upper half of FIGS. 2a to 2c, of the clamping sleeve 28.

A conical actuating surface 70 is incorporated in the inner surface of the hollow shaft 22, and widens in the same direction as the conical surfaces 66 and 68 of the spring tongues 62 and 64, namely from top to bottom in FIG. 1, and co-operates therewith. The axial extension of the conical actuating surface 70 of the hollow shaft 22 is however somewhat longer than that of the conical surfaces 66 and 68 of the spring tongues 62 and 64, so that the conical surfaces 66 and 68 of the spring tongues 62 and 64 under axial movement of the clamping sleeve 28 remain substantially in contact with the conical actuating surface 70 of the hollow shaft 22. In the embodiment of the hollow shaft illustrated in the drawing, the lower edge of the conical surface 70 is formed by a groove-shaped undercut 72.

The axial positions of the conical actuating surface 70 of the hollow shaft 22 and of the conical surfaces 66 and 68 of the spring tongues 62 and 64 are matched to one another in the following way:

In the clamping position of the clamping sleeve 28 shown in the drawing, in which therefore this sleeve adopts its axially uppermost position, the conical actuating surface 70 has radii that are smaller than the corresponding radii of the conical surface 66 and 68 on the undeformed spring tongues 62 and This means that the clamping sleeve 28 can only adopt the position illustrated in FIG. 1 if the spring tongues 62 and 64 are elastically pressed inwardly.

Finally, a ring gear 74 is formed on the outer surface of the hollow shaft 22, which meshes with the toothed gear 16 on the drive shaft 14. When the drive shaft 14 turns the hollow shaft 22 is thereby caused to rotate in the ball bearing arrangements 24 and 26.

The dental instrument holder 10 described above functions a follows:

To insert a dental instrument, for example a drill (not shown in the drawing), the press button 40 is pressed downwardly by the user and in this way the clamping sleeve 28 is displaced downwardly. As a result of this axial movement of the clamping sleeve 28 the conical surfaces 66 of the spring tongues 62 and 64 are now in a region of the conical actuating surface 70 of the hollow shaft 22 that in general is of larger radius. The lower ends of the spring tongues 62 and 64 can now therefore bend radially outwards. In this position the shank of the dental instrument can be inserted from below into the hollow shaft 22 and into the interior of the clamping sleeve 28 until the upper end of this shank comes into contact with a shoulder 78 of the continuous bore 76 of the clamping sleeve 28. The user now releases the pressure on the press button 40; the compression spring 30 urges the clamping sleeve 28 within the hollow shaft 22 upwardly to the position shown in FIG. 1. Through the co-operation of the conical actuating surface 70 on the inside of the hollow shaft 22 and the conical surfaces 66 and 68 on the clamping sleeve 28, the lower ends of the spring tongues 62 and 64 are urged inwardly against the surface of the shank of the instrument, the latter thereby being clamped against the clamping sleeve 28.

If the drive shaft 14 and thus the hollow shaft 22 is now caused to rotate, the dental instrument together with its shank is now in an optimum position, and to be more precise with its upper region inside the clamping sleeve 28 and its lower region in the lower outlet opening 80 of the hollow shaft 22. Since the clamping sleeve 28 is for its part reliably positioned and mounted at both axial ends within the hollow shaft 22, the dental instrument is now in this way guided so precisely that no imbalance or eccentricity can occur. This is attributed in particular to the fact that the middle, elastically sprung clamping region 56 of the clamping sleeve 28 is not involved in the bearing function.

Figure 3:
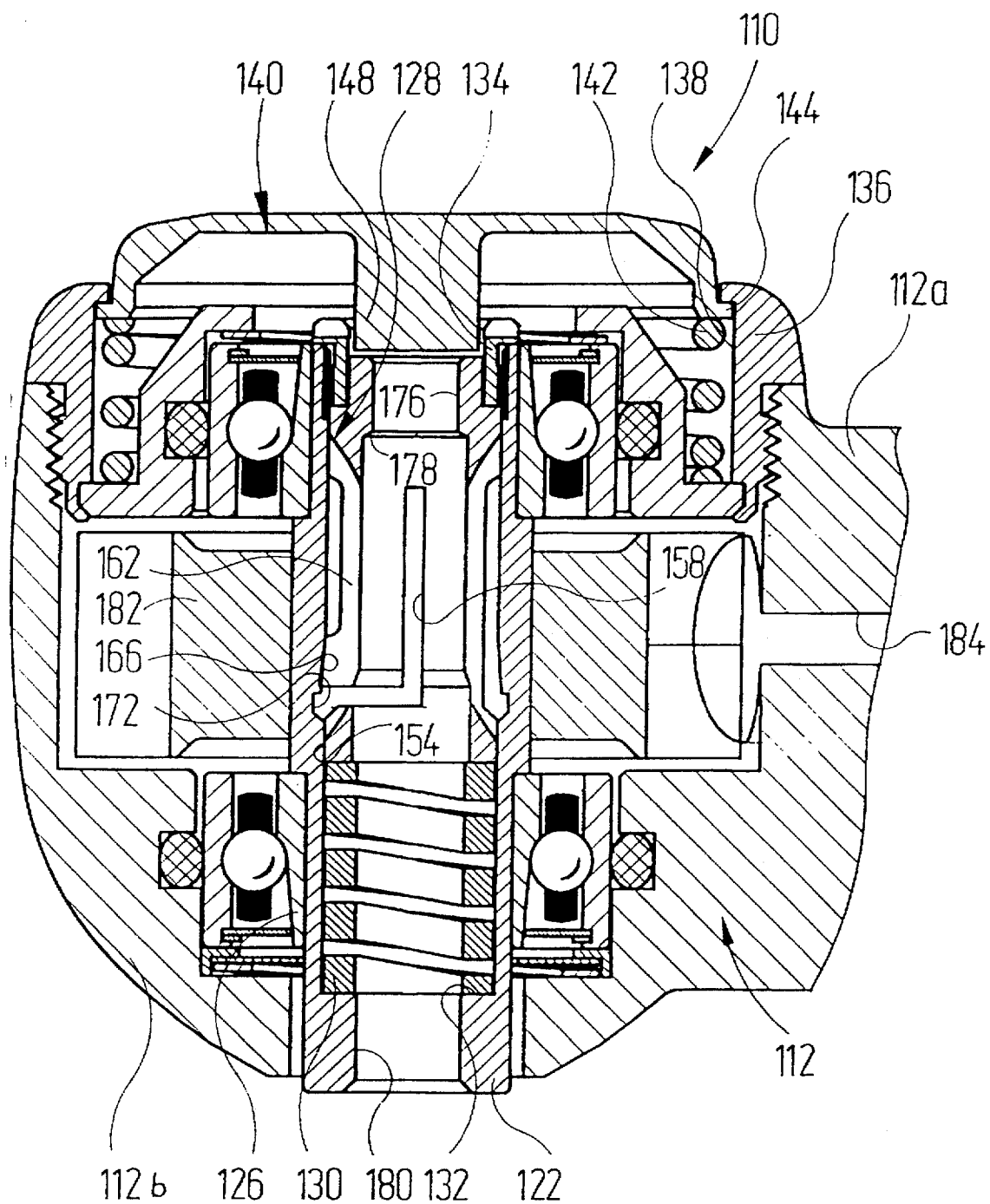
FIG. 3 is a section, similar to FIG. 1, through a second embodiment of a dental instrument holder.

FIG. 3 shows a second embodiment of a dental instrument holder, which is very similar to that described above with the aid of FIGS. 1 and 2. Corresponding parts are therefore identified by the same reference numerals plus 100. The main difference between the two embodiments is the type of drive: whereas in the first embodiment the hollow shaft 22 is caused to rotate by a drive shaft 14 passing through the handle region 12a, via an angular gear, the embodiment according to FIG. 3 is provided with a turbine.

The embodiment of a dental instrument holder illustrated in FIG. 3 also comprises a housing 112 with a handle region 112a and a head region 112b. The head region 112b is closed at the top by a removable cover 120, which in this case dovetails with a screw ring 136 securing the cover 120 in the housing 112.

A hollow shaft 122 is mounted in the region of its upper end in a first ball bearing arrangement 124 secured on the cover 120, and in the region of its lower end in a second ball bearing arrangement 126 secured on the housing 112. The interior of the hollow shaft 122 accommodates in axial alignment, in complete conformity with the embodiment of FIG. 1, a compression spring 130 as well as a clamping sleeve 128. The clamping sleeve 128 is identical to the clamping sleeve 28 of the embodiment of FIG. 1.

Turbine blades 182 are formed on the outer surface of the hollow shaft 122, which are actuated by compressed air flowing through a compressed air channel 184 passing through the handle region 112a of the housing 12.

The clamping and release of a dental instrument in the hollow shaft 122 and in the clamping sleeve 128 is carried out in a completely identical manner to the corresponding procedures in the embodiment according to FIG. 1.

The compression springs 30 and 130 used in both embodiments and that engage the clamping sleeve 28 and 128 respectively are not, as is normally the case, fabricated from spring wire but instead from a cylindrical sleeve of spring material in which a helical slit or notch is made.

What is claimed is:

1. Dental instrument holder which comprises:

a) a housing comprising a head region and a handle region;

b) a driven hollow shaft rotatably mounted in the head region of the housing and designed to receive the shank of a dental instrument;

c) a clamping sleeve arranged within the hollow shaft into which sleeve the end region of the shank of the dental instrument can be inserted and which has at least one spring-loaded clamping region;

d) a conical actuating surface on a structural element adjacent to the clamping sleeve and which co-operates with the spring-loaded clamping region of the clamping sleeve, wherein e) the structural element carrying the conical actuating surface and the clamping sleeve being arranged such that there is a reciprocating relative movement between two axial positions, namely ea) a clamping position in which the spring-loaded clamping region of the clamping sleeve is urged radially inwardly by the conical actuating surface;

eb) a release position in which the spring-loaded clamping region of the clamping sleeve is urged in a radial direction under the action of the spring in which the clamping sleeve has two cylindrical annular closed bearing regions axially spaced apart, between which the spring-loaded clamping region is arranged.

2. A dental instrument holder as claimed in claim 1, wherein the spring-loaded clamping region of the clamping sleeve has at least one spring tongue which is formed by a U-shaped incision or notch cut from the clamping sleeve.

3. A dental instrument holder as claimed in claim 2, wherein two diametrically opposite spring tongues are provided.

4. A dental instrument holder as claimed in claim 2, wherein each spring tongue has at its free end a conical surface that co-operates with the conical actuating surface of the adjacent structural part.

5. A dental instrument holder as claimed in claim 1, wherein a groove-shaped undercut is provided on an edge having the larger diameter of the conical actuating surface of the structural part adjacent to the clamping sleeve.

6. A dental instrument holder as claimed in claim 1, in which the clamping sleeve is urged by a compression spring in the direction of the clamping position, wherein the compression spring is formed by a sleeve of spring material through which a helical incision or indent is cut.

* * * * *